(12) United States Patent
Chablat et al.

(10) Patent No.: US 12,161,514 B2
(45) Date of Patent: Dec. 10, 2024

(54) SURGERY-ASSISTANCE DEVICE (71) Applicants: CENTRE NATIONAL DE LA RECHERCHE SCIENTIFIQUE—CNRS, Paris (FR); CHU DE NANTES, Nantes (FR)

(72) Inventors: Damien Chablat, La Chapelle sur Erdre (FR); Guillaume Michel, Saint Sebastien sur Loire (FR); Philippe Bordure, Nantes (FR)

(73) Assignees: CENTRE NATIONAL DE LA RECHERCHE SCIENTIFIQUE—CNRS, Paris (FR); CHU DE NANTES, Nantes (FR)

( * ) Notice: Subject to any disclaimer, the term of this patent is extended or adjusted under 35 U.S.C. 154(b) by 448 days.

(21) Appl. No.: 17/762,614

(22) PCT Filed: Sep. 22, 2020

(86) PCT No.: PCT/EP2020/076353
§ 371 (c)(1),
(2) Date: Mar. 22, 2022

(87) PCT Pub. No.: WO2021/058448
PCT Pub. Date: Apr. 1, 2021

(65) Prior Publication Data
US 2022/0338954 A1 Oct. 27, 2022

(30) Foreign Application Priority Data
Sep. 24, 2019 (FR) ........................ 1910523

(51) Int. Cl.
*A61B 90/50* (2016.01)
*B25J 19/00* (2006.01)

(52) U.S. Cl.
CPC ........... *A61B 90/50* (2016.02); *B25J 19/0016* (2013.01); *A61B 2090/506* (2016.02)

(58) Field of Classification Search
CPC ... A61B 90/50; A61B 90/10; A61B 2090/506; B25J 19/0016
See application file for complete search history.

(56) References Cited

U.S. PATENT DOCUMENTS 5,397,323 A * 3/1995 Taylor ................... A61B 34/71
901/41
5,817,084 A 10/1998 Jensen
(Continued)

FOREIGN PATENT DOCUMENTS

DE 69310085 T2 10/1997
FR 2845889 A1 4/2004

OTHER PUBLICATIONS

Oct. 15, 2020 International Search Report issued in International Patent Application No. PCT/EP2020/076353.
(Continued)

*Primary Examiner* — Brooke Labranche
(74) *Attorney, Agent, or Firm* — Williams Mullen; R. Brian Drozd (57) ABSTRACT

A device for assisting surgery includes means for offsetting a rotation of a first type and a second type, a mechanism for transmitting a rotation of a third type, and a mechanism for transforming the rotation of a third type into a translation. An elastic element is connected at one end to the mechanism for transmitting the rotation of a third type. The mechanism for transmitting the rotation of a third type is connected to a rotary motor, the rotation of the motor in a first direction causing the lowering of a tool and an elongation of the elastic element, the rotation of the motor in a second direction causing the raising of the tool and a contraction of the elastic element, and, when the tool is lowered and the
(Continued)

rotary motor is not exerting any torque, the elastic element returns to an initial shape causing the raising of the tool.

12 Claims, 4 Drawing Sheets

(56) References Cited

U.S. PATENT DOCUMENTS

| | | | |
|---|---|---|---|
| 2004/0024385 A1* | 2/2004 | Stuart | B25J 9/1065 606/1 |
| 2016/0346940 A1* | 12/2016 | Bax | A61B 34/30 |
| 2019/0053863 A1* | 2/2019 | Hongo | A61B 34/30 |

OTHER PUBLICATIONS

Oct. 15, 2020 Written Opinion issued in International Patent Application No. PCT/EP2020/076353.

\* cited by examiner

SURGERY-ASSISTANCE DEVICE

TECHNICAL FIELD

The present invention relates to the field of assistance in surgery. The present invention relates more precisely to the field of surgical robots intended for assisting a surgeon during surgery.

PRIOR ART

During a surgical operation, a surgeon generally uses both hands to hold, in one hand a surgical instrument and in the other a suction tool. In some cases, the surgical operations are performed in operative fields that are difficult to access and which are not fully observable from outside with a microscope or a binocular magnifier. This is the case for example in ear surgery since the ear comprises a narrow auditory canal behind which a wider cavity is located. In order to view the entire operative field, the surgeon must then have recourse to the use of an endoscope. As a corollary, the surgeon must release the suction tool, which is also a problem. This is because, when the operation causes significant bleeding, as is often the case in ear surgery, the absence of a suction tool impairs visibility and means that the endoscope must be frequently removed to be cleaned. Repeating insertions and extractions of the endoscope during the operation requires precision and is time wasting for the surgeon. Moreover, some incidents may occur during an operation, such as for example the patient waking up, requiring removing the endoscope in a secure manner and as quickly as possible in order to avoid injuring the patient.

It is desirable to overcome these drawbacks of the prior art. It is in particular desirable to provide a solution that makes it possible to insert and extract an endoscope in a difficult-to-access operative field in an automated, reliable and secure manner. It is in particular desirable to provide a solution that makes it possible to keep and orient an endoscope in an operative field while limiting the occupation of the working space of the surgeon above the patient. It is also desirable to provide a solution that allows rapid and automatic extraction of the endoscope in the event of the occurrence of an incident and which furthermore makes it possible to reinsert the endoscope with precision at a previous position.

DISCLOSURE OF THE INVENTION

One object of the present invention is to propose a surgery-assistance device comprising means for offsetting a rotation of a first type and a rotation of a second type and furthermore comprising a mechanism for transmitting a rotation of a third type and a mechanism for transforming the rotation of a third type into a translation. Said translation is enabled along an insertion axis oriented in a direction defined by the means for offsetting the rotation of a first type and the rotation of a second type. The mechanism for transmitting the rotation of a third type is connected to a first end of an elastic element, and the second end of the elastic element is connected to the means for offsetting the rotation of a first type and the rotation of a second type. The mechanism for transmitting the rotation of a third type is connected to a rotary motor, the rotation of the rotary motor in a first direction causing the lowering of a tool carried by the surgery-assistance device and a first deformation of the elastic element, the rotation of the rotary motor in a second direction causing the raising of the tool and a second deformation of the elastic element opposite to the first deformation, the tool remaining in a given position as long as a torque exerted by the rotary motor is maintained and, when the tool is in a lowered position and the rotary motor is not exerting any torque, the elastic element returns to an initial shape causing the raising of the tool.

Thus the tool can be inserted into and extracted from the surgical field in a reliable and automated manner and the tool can be extracted in a secure and rapid manner in the event of an incident.

According to a particular embodiment, the first deformation is an elongation.

Thus the elastic element generates a traction on the mechanism for transmitting the rotation of a third type that tends to drive said rotation of a third type in a direction causing the raising of the tool and therefore the extraction thereof from the surgical field.

According to a particular embodiment, the means for offsetting the rotation of a first type and the rotation of a second type comprise two parallelograms connected together and a device for actuating the rotation of a third type and the rotation of a second type. The actuation device generates a rotation movement of a first type, about a first axis, of a rod of a parallelogram with respect to another rod of said parallelogram, and generates a rotation movement of a second type, about a second axis, of the two parallelograms with respect to a base of the surgery-assistance device, the first axis being perpendicular to the second axis, and the rotation movements of a first type and of a second type being transmitted by the two parallelograms at an offset centre of rotation.

Thus the tool can be held and oriented in an automated manner in the surgical field by means of the offsetting of the centre of rotation while limiting the occupation of a working space of the surgeon, located above the surgical field.

According to a particular embodiment, the actuation device comprises two other rotary motors, each of the rotations of a first and second type being actuated by one of the other two rotary motors.

Thus the orientation of the tool is actuated remotely.

According to a particular embodiment, the actuation device comprises two linear motors, the rotations of a first and second type being actuated by the conjoint action of the two linear motors.

Thus the orientation of the tool is actuated remotely.

According to a particular embodiment, the mechanism for transmitting the rotation of a third type comprises a third parallelogram. The rotary motor generates a rotation movement of a third type, about a third axis, of a first rotary element with respect to the means for offsetting the rotation of a first type and the rotation of a second type, the rotation movement of a third type being transmitted by the third parallelogram to a second rotary element, about a fourth axis parallel to the third axis.

Thus the tool can be inserted into and extracted from the surgical field by means of a remote actuation, which limits the occupation of the working space of the surgeon.

According to a particular embodiment, the mechanism for transmitting the rotation of a third type comprises a belt. The rotary motor generates a rotation movement of a third type, about a third axis, of a first rotary element with respect to the means for offsetting the rotation of a third type and the rotation of a second type, the rotation movement of a third type being transmitted by the belt to a second rotary element, about a fourth axis parallel to the third axis.

Thus the tool can be inserted into and extracted from the surgical field by means of a remote actuation, which limits the occupation of the working space of the surgeon.

According to a particular embodiment, the mechanism for transforming the rotation of a third type into a translation comprises a connecting rod. The head of the connecting rod is connected to the mechanism for transmitting the rotation of a third type and the foot of the connecting rod is connected to the tool and to the means for offsetting the rotation of a first type and the rotation of a second type, and, when the rotation movement of a third type is transmitted to the head of the connecting rod, the foot of the connecting rod transmits to the tool a translation movement along the insertion axis.

Thus the tool is always oriented in the direction of the insertion axis and can be inserted into and extracted from the surgical field at any moment without risking damaging a narrow passage space, such as an auditory canal.

According to a particular embodiment, the mechanism for transforming the rotation of a third type into a translation comprises a toothed wheel connected to the mechanism for transmitting the rotation of a third type and comprises a rack secured to a tool holder to which the tool is connected, the toothed wheel being connected to the rack by gearing so that, when the toothed wheel begins to move in the rotation of a third type, the tool makes a translation movement along the insertion axis.

Thus the tool is always oriented in the direction of the insertion axis and can be inserted into and extracted from the surgical field at any moment without risking damaging a narrow passage space, such as an auditory canal.

According to a particular embodiment, the means for offsetting the rotation of a first type and the rotation of a second type are connected to a movable base, the movable base being able to be moved and secured to an operating table in accordance with three translation axes perpendicular to each other.

Thus the surgery-assistance device can be moved with precision on an operating table prior to surgery so that the tool is positioned above the surgical field.

According to a particular embodiment, the surgery-assistance device furthermore comprises a mechanism for rotating the tool about the insertion axis.

Thus the tool can turn on itself in the surgical field and observe a cavity at different viewing angles, particularly in the case of an endoscope where the central direction of the viewing field is different from 0° with respect to the insertion axis of the tool.

According to a particular embodiment, the tool is an endoscope for assisting ear and sinus surgery.

According to a particular embodiment, the surgery-assistance device furthermore comprises a control means actuated by an individual and cancelling out the torque exerted by the rotary motor so that, if the tool is in a lowered position, the elastic element returns to the initial shape causing the raising of the tool.

BRIEF DESCRIPTION OF THE DRAWINGS

The features of the invention mentioned above, as well as others, will emerge more clearly from the reading of the following description of at least one example embodiment, said description being made in relation to the accompanying drawings, among which.

DETAILED DISCLOSURE OF EMBODIMENTS

Figure 1:
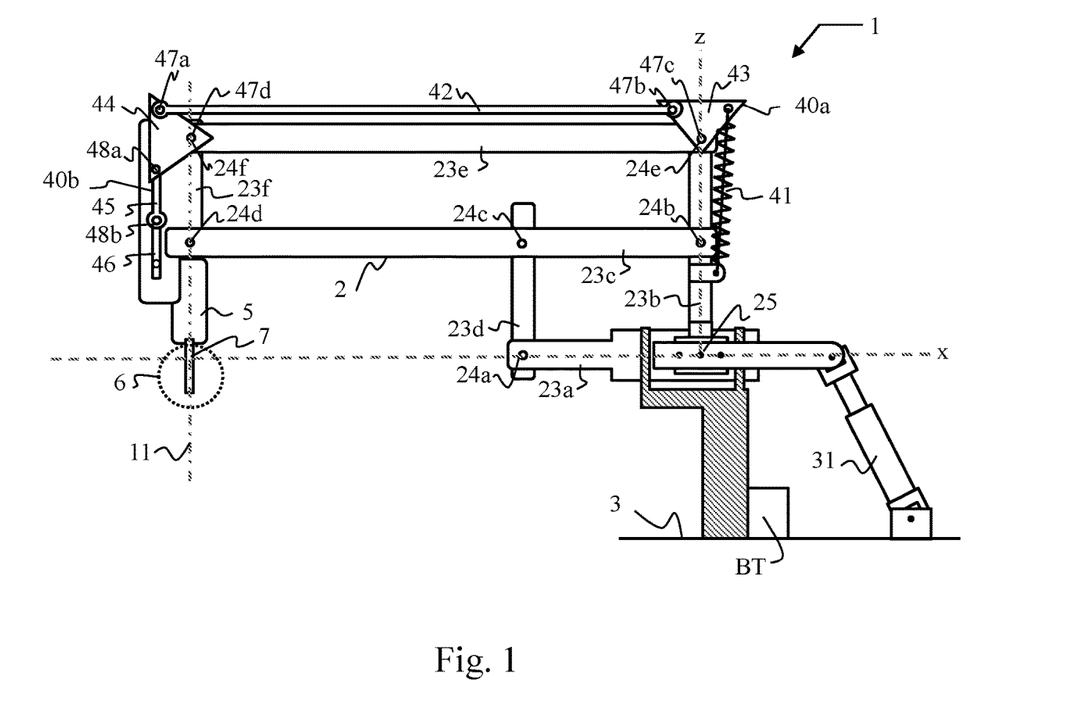
FIG. 1 schematically illustrates a side view of a robot intended to assist surgery according to the present invention comprising a base, an arm and a system for inserting and extracting a tool, the insertion/extraction system being in a position such that the tool is lowered and located in a surgical field.

FIG. 1 schematically illustrates a side view of a robot 1 or device for assisting ear surgery comprising a system for inserting and extracting a tool 5 such as for example an endoscope. The insertion/extraction system is in a position such that the tool 5 is lowered and located in a surgical field 6. The robot 1 comprises a base 3, an arm 2, the insertion/extraction system and the tool 5. The robot 1 is shown schematically in a reference frame (Oxyz), the point O being located at the intersection of an axis (Ox) and of an axis (Oz) and an axis (Oy) being perpendicular to the plane (Oxz). The surgical field 6 is situated in proximity to the intersection between an insertion axis 11 and the axis (Ox).

The arm 2 of the robot 1 comprises a double deformable parallelogram composed of a first parallelogram comprising four rods 23a, 23b, 23c, 23d and connected to a second parallelogram comprising four rods 23b, 23c, 23e, 23f. The vertical rear rod 23b and the horizontal intermediate rod 23c are common to the two parallelograms. The rods 23a to 23f are connected together by pivot connections 24a to 24f allowing rotations of axes parallel to the axis (Oy) as well as a connection 25 concretised by a cardan drive and allowing in particular a rotation of axis (Oy) between the bottom rod 23a and the rear rod 23b. The insertion axis 11 of the tool 5 is oriented in the direction of the front rod 23f, parallel to the rear rod 23b and vertical intermediate rod 23d.

Figure 3:
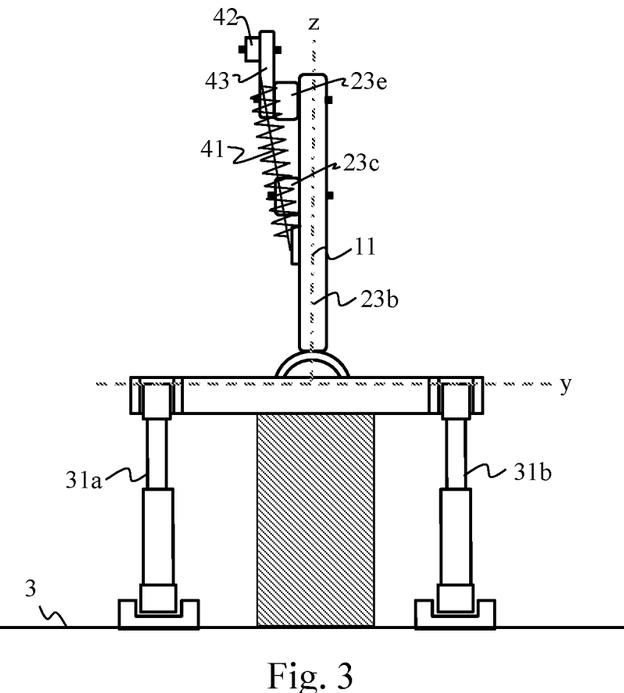
FIG. 3 schematically illustrates a rear view of the robot.
Figure 4:
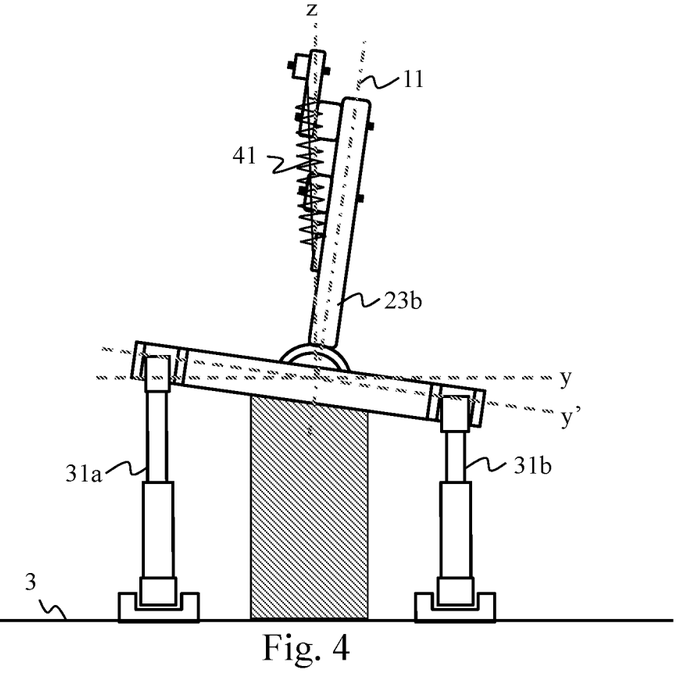
FIG. 4 schematically illustrates in rear view the robot the arm of which has a tilt connected to a rotation of a second type, of axis (Ox)

The arm 2 of the robot 1 is connected to the base 3 by an actuation mechanism for actuating two rotations of the rear rod 23b with respect to the base 3: a rotation of a first type, of axis (Oy), and a rotation of a second type, of axis (Ox). Each of the rotations of a first and second type can be actuated independently and the two rotations of a first and second type can be combined. According to a particular embodiment presented in FIG. 1, the actuation of the rotations of a first and second type, of axis (Oy) and of axis (Ox), is implemented by means of the conjoint action of two parallel linear motors 31. The linear motors 31a and 31b are also shown in FIGS. 3 and 4. Alternatively, the actuation of each of the rotations of a first type and of a second type is implemented by means of a rotary motor. Furthermore, the arm 2 of the robot 1 is connected to the base 3 by a pivot connection of axis (Ox) between the bottom rod 23a and the base 3, making it possible to eliminate degrees of freedom, and in particular to prevent a rotation of axis (Oy) between the bottom rod 23a and the base 3 so that the bottom rod 23a remains permanently horizontal, in line with the axis (Ox).

When the rotation of a second type is actuated by the actuation mechanism, the rear rod 23b drives the whole of the arm 2 of the robot 1 in the rotation movement of a second type, because of the absence of a degree of freedom on the rotation axis (Ox) between the rear rod 23b and the rods 23c, 23d, 23e, 23f of the arm 2. The insertion axis 11 thus follows the movement of the rotation of a second type about a point, referred to as the offset centre of rotation 7, and located on the axis (Ox) at the intersection of the insertion axis 11. The tilt of the arm 2 and of the insertion axis 11 thus obtained can be observed in FIG. 4 in comparison with the position of the arm 2 in FIG. 3. When the arm is tilted, the pivot connections 24a to 24f allow rotations of axes parallel to an axis (Oy'), the axis (Oy') being the image of the axis (Oy) by the rotation of a first type, as presented in FIG. 3.

When the rotation of a second type, of axis (Oy), is actuated by the actuation mechanism, the rotation movement is transmitted to the front rod 23f. The front rod 23f then makes a rotation about an axis parallel to (Oy) centred on the offset centre of rotation 7. The inclination of the insertion axis 11 thus obtained can be observed in FIG. 2, in comparison with the position of the insertion axis 11 in FIG. 1.

The arm 2 of the robot 1 makes it possible to offset the two rotations of a first and second type from the actuation mechanism, located at a distance from a working space of the surgeon, towards the offset centre of rotation, located at the surgical field 6. The occupation of the working space of the surgeon is thus limited.

The insertion/extraction system comprises an elastic element such as for example a spring 41, a mechanism 40a for transmitting a rotation of a third type and a mechanism 40b for transforming the rotation of a third type into translation. The insertion/extraction system furthermore comprises an actuator, such as for example a rotary motor for exerting a torque on a first rotary element 43 of the transmission mechanism 40a of the rotation of a third type. A first end of the spring 41 is connected to a vertical rod of the arm 2, such as the rear rod 23b or the rod 23d, and a second end of the spring 41 is connected to the first rotary element 43.

The mechanism 40a for transmitting the rotation of a third type comprises a third deformable parallelogram comprising at least a part of the top rod 23e of the double parallelogram, a supplementary rod 42 parallel to said top rod 23e, the first rotary element 43 and a second rotary element 44. The first and second rotary elements 43 and 44 each have at least two assembly zones enabling them to be connected to the rods 23e and 42. The assembly zones are spaced apart by the same distance for each rotary element 43, 44 and are for example cylindrical cavities with parallel axes. More precisely, the first assembly zone of the first rotary element 43 is connected to a first point on the top rod 23e by a pivot connection 47c, with its axis parallel to (Oy'), enabling the first rotary element 43 to turn with respect to the top rod 23c in a rotation movement of a third type. In a similar manner, the first assembly zone of the first rotary element 44 is connected to a second point on the top rod 23e by means of a pivot connection 47d, with its axis parallel to (Oy'). The supplementary rod 42 is connected at a first end to the second assembly zone of the first rotary element 43 by a pivot connection 47b, and at a second end to the second assembly zone of the third rotary element 44 by a pivot connection 47a. The pivot connections 47a and 47b allow rotations about axes parallel to (Oy'). Thus a rotation movement of a third type of the rotary element 43 with respect to the top rod 23e, generated at the pivot connection 47c for example by a rotary motor, is transmitted to the rotary element 44 at the pivot connection 47d. The rotary element 44 then follows a rotation movement parallel to and of the same amplitude as the rotary element 43, and the actuator is offset towards the base 3, leaving a larger working space above the surgical field 6.

According to a particular embodiment that is not illustrated here, the mechanism 40a for transmitting the rotation of a third type comprises a belt connecting the first rotary element 43 and the second rotary element 44 around axes corresponding to the pivot connections 47c and 47d. Said belt can thus transmit a rotation movement of a third type without requiring a supplementary rod 42.

Moreover, the first end of the spring 41 is connected to a third assembly zone of the rotary element 43, the third assembly zone being positioned so that, when the rotary element turns in an anticlockwise direction with respect to the top rod 23e, the spring 41 is stretched and exerts a traction force between the rotary element 43 and a fastener secured to the rear rod 23b, the traction force tending to cause the rotary element 43 to begin to rotate in a clockwise direction.

According to a preferential embodiment, the first end of the spring 41 is connected to the rear rod 23b and the first assembly zone of the first rotary element 43 is connected to the rear end of the top rod 23e. Thus the mass of the insertion/extraction system and the actuator are mainly offset close to the base 3 and as far away as possible from the surgical field 6.

According to a particular embodiment, the mechanism 40b for transforming the rotation of a third type into translation comprises a connecting rod 45. The head of the connecting rod 45 is connected to a third assembly zone of the rotary element 44 by a pivot connection 48a. The foot of the connecting rod 45 is connected to the front rod 23f by a pivot connection 48b with its axis parallel to (Oy') associated with a sliding connection 46 with a guide axis parallel to the insertion axis 11. The sliding connection 46 can be concretised by a slot hollowed in the front rod 23f. The rotation movement of a third type of the rotary element 44 is thus transformed into a translation movement parallel to the insertion axis 11. Said translation movement is transmitted to the tool 5, which is connected both to the front rod 23f by the sliding connection 46 and to the foot of the connecting rod 45. The tool 5 can thus be raised or lowered by translation along the insertion axis 11.

When the tool 5 is inserted into the surgical field 6, an actuator, such as a rotary motor, applies a torque to the rotary element 43 about the rotation axis of the pivot connection 47c in an anticlockwise direction. The rotation of a third type of the rotary element 43 causes firstly the elongation of the spring 41 under traction. Secondly, the rotation of a third type of the rotary element 43 is transmitted to the rotary element 44 about the axis of the pivot connection 47 and transformed, by the connecting rod 45 connected to the front rod 23f, into downward translation on an axis parallel to the insertion axis 11. The tool 5 is thus lowered into the surgical field 6 while following the insertion axis 11. The torque applied by the actuator is maintained throughout the period of use of the tool 5 so that the tool 5 remains in a lowered position.

When a torque is applied by the actuator to the rotary element 43 in a clockwise direction, the mechanism of the insertion/extraction system causes conversely the lifting of the tool 5 and the contraction of the spring 41. The position of the insertion/extraction system and the raised position of the tool 5 then obtained are presented in FIG. 5.

When the torque applied by the actuator is zero and the tool 5 is in a lowered position, the traction force exerted by the spring 41 on the rotary element 43 causes the rotation of the rotary element 43 about the rotation axis of the pivot connection 47c in a clockwise direction until the spring 41 returns to its initial position. Said rotation in a clockwise direction is transmitted to the rotary element 44 and then transformed into a translation movement, directed upwards, making it possible to raise the tool 5 along the insertion axis 11. The tool 5 can thus be extracted at any moment from the surgical field 6 with a response time that is as quick as possible, related solely to the reaction time of the spring 41. The extraction of the tool 5 is furthermore made secure and occurs automatically as soon as the actuator generating the torque applied to the rotary element 43 is stopped, for example when the current is cut off. An emergency stop button BT, such as a mushroom-type button, can be actuated by an individual and makes it possible to mechanically trigger an extraction command that cuts off the actuator generating the torque applied to the rotary element 43. Through the effect of the spring 41, the extraction command causes the raising of the tool 5 automatically. It is thus possible to extract the tool 5 from the surgical field in a secure and rapid manner when there is an unexpected incident. In particular, the emergency stop button can be used when a patient wakes up during the surgery or when the current is cut off. In a particular embodiment, the extraction command is connected to a system for monitoring the patient and is triggered when the monitoring system detects that the patient is waking up.

According to a particular embodiment, the elastic element of the insertion/extraction system is a torsion spring.

Since the connection between the tool 5 and the front rod 23f does not allow a rotation movement about the axes (Ox) and (Oy), the tool 5 remains oriented along the insertion axis 11 in the direction of the front rod 23f at all times and whatever the position of the insertion/extraction system. Thus the tool 5 can easily be oriented around the offset centre of rotation 7 during surgery and it is possible to extract the tool 5 from the surgical field 6 in a reliable manner at any moment, without risking damaging a narrow passage space, such as an auditory canal. It is also possible to extract and then reinsert the tool 5 in the surgical field 6 while keeping the position and the orientation of the tool 5. For example, the tool 5 can be extracted from the surgical field in order to perform a cleaning operation, and then reinserted in the surgical field 6 precisely and automatically, at the same position and with the same orientation as before the extraction.

The tool 5 is preferentially a surgery-assistance tool that does not come into contact with the human body. Thus the forces and torques transmitted by the insertion/extraction system remain low and are dependent mainly on the stiffness of the spring 41.

According to a particular embodiment, not illustrated here, the base 3 is movable or attached to a movable device allowing three translations: a translation along the axis (Ox), a translation along the axis (Oy) and a translation of axis (Oz). Thus the robot 1 can be moved on an operating table prior to surgery so that the tool is positioned above the surgical field 6.

According to a particular embodiment, not illustrated here, the robot 1 furthermore comprises a mechanism for rotating the tool 5 about the insertion axis 11. Said rotation mechanism comprises a first toothed wheel with its axis parallel to (Oy') connected by gearing to a second toothed wheel rotating about the insertion axis 11. The first toothed wheel is connected to the front rod 23f and to the rotary element 44, by a pivot connection, coaxial with the pivot connections 24f and 47d. The second toothed wheel is attached to a tool holder, connected to the front rod 23f by the sliding connection 46 and to the foot of the connecting rod 45 by a pivot connection 48h. The tool 5 is attached to the tool holder. When the first toothed wheel starts to rotate about an axis parallel to (Oy'), it causes a rotation movement of the tool holder and therefore of the tool 5 about the insertion axis 11. Thus it is possible to orient the tool by a rotation about the insertion axis 11 independently of the rotation movements of a first and second type and independently of the low or raised position of the tool 5. This makes it possible for example to observe the surgical field 6 at various angles in the case where the tool 5 is an endoscope the field of view of which is not centred on 0°.

The rotation movement of the first toothed wheel is preferentially actuated in an offset manner. For example, the use of a belt makes it possible to connect the first toothed wheel to an additional actuator, such as a rotary motor, itself connected to the rear rod 23b and to the rotary element 43 by a pivot connection coaxial with the pivot connections 24e and 47c.

Figure 2:
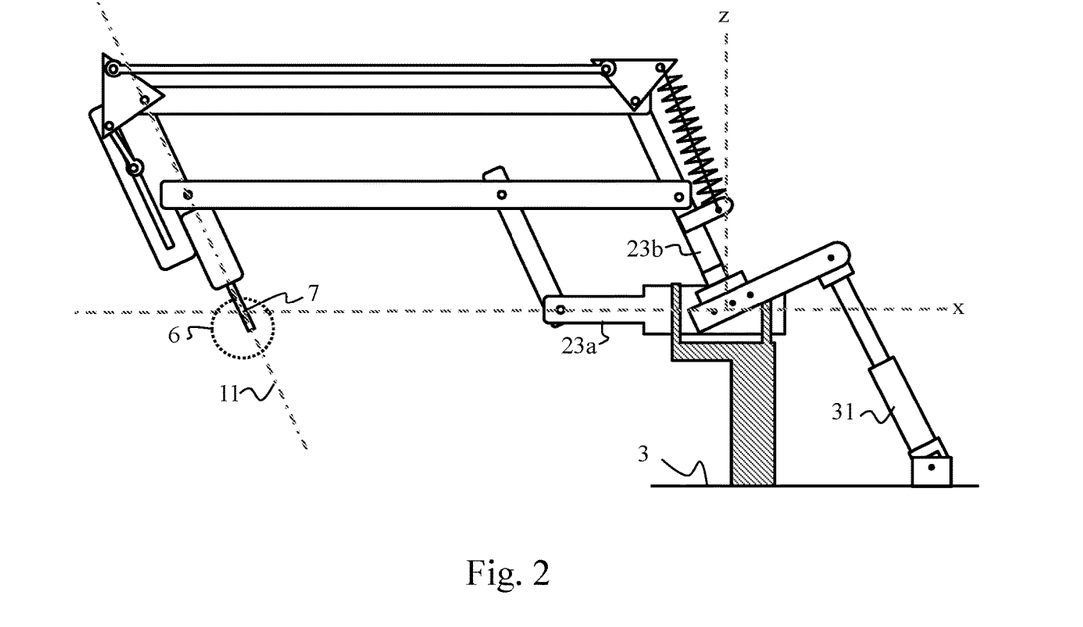
FIG. 2 schematically illustrates a side view of the robot the arm of which has a tilt connected to a rotation of a first type, of axis (Oy)

FIG. 2 schematically illustrates a side view of the robot 1 in a position where the insertion axis 11 has a tilt connected to the rotation of the first type of axis (Oy). The two linear motors 31 actuate the rotation of a first type of the rear rod 23b with respect to the base 3 of the robot 1. The tilt obtained is transmitted to the front rod 23f and to the insertion axis 11 of the tool 5, the initial centre of rotation O being offset from the offset centre of rotation 7 situated at the intersection of the axis (Ox) and of the insertion axis 11.

FIG. 3 schematically illustrates the robot 1 intended to assist the surgery in rear view.

The two linear motors 31a and 31b connect the base 3 to the rear rod 23b of the arm 2 by a connection making it possible to actuate the rotations of a first and second type, respectively of axis (Ox) and of axis (Oy). The axis (Ox) is perpendicular to the plane (Ozy), in other words to the plane of the sheet.

The rear rod 23b of the parallelogram is connected to the horizontal intermediate rod 23c and to the top rod 23e by the respective pivot connections 24b and 24e parallel to the axis (Oy). The first assembly zone of the rotary element 43 is connected to the top rod 23e, the second assembly zone of the rotary element 43 is connected to the supplementary rod 42 and the third assembly zone of the rotary element 43 is attached to the second end of the spring 41. The first end of the spring 41 is attached to the rear rod 23b.

FIG. 4 schematically illustrates in rear view the robot 1 in a position where the insertion axis 11 has a tilt connected to the rotation of a second type of axis (Ox). The two linear motors 31 actuate the rotation of a second type of the rear rod 23b with respect to the base 3 of the robot 1. The tilt of the rear rod 23b thus obtained is transmitted to the whole of the arm 2 and to the insertion axis 11. The axis (Oy') is the image of the axis (Oy) through the rotation of axis (Ox) made.

Figure 5:
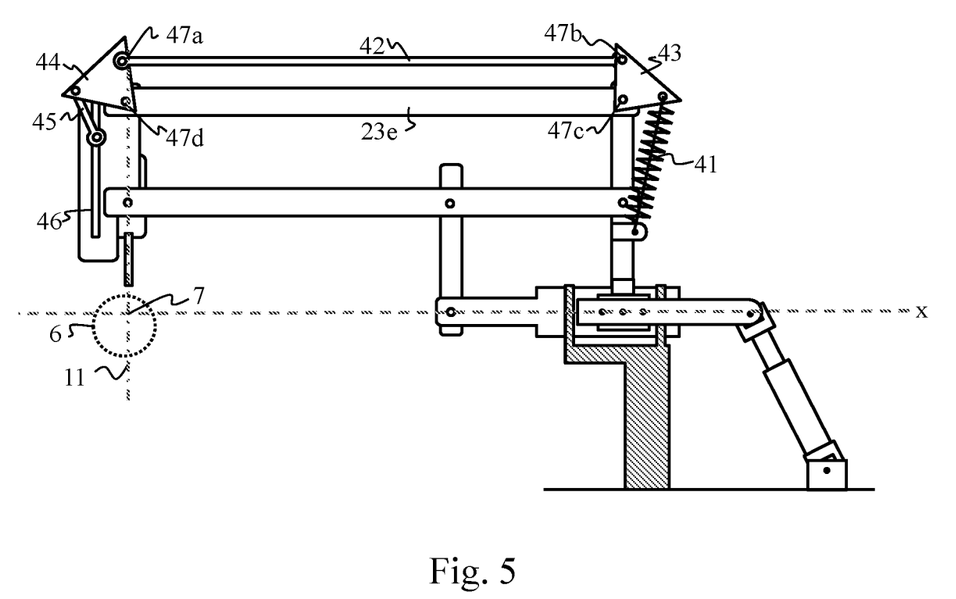
FIG. 5 schematically illustrates the robot in side view, the insertion/extraction system being presented in a raised position with the tool located outside the surgical field.

FIG. 5 schematically illustrates the robot 1 in side view, the insertion/extraction system being presented in a raised position where the tool 5 is outside the surgical field 6. The spring 41 is not deformed.

Figure 6:
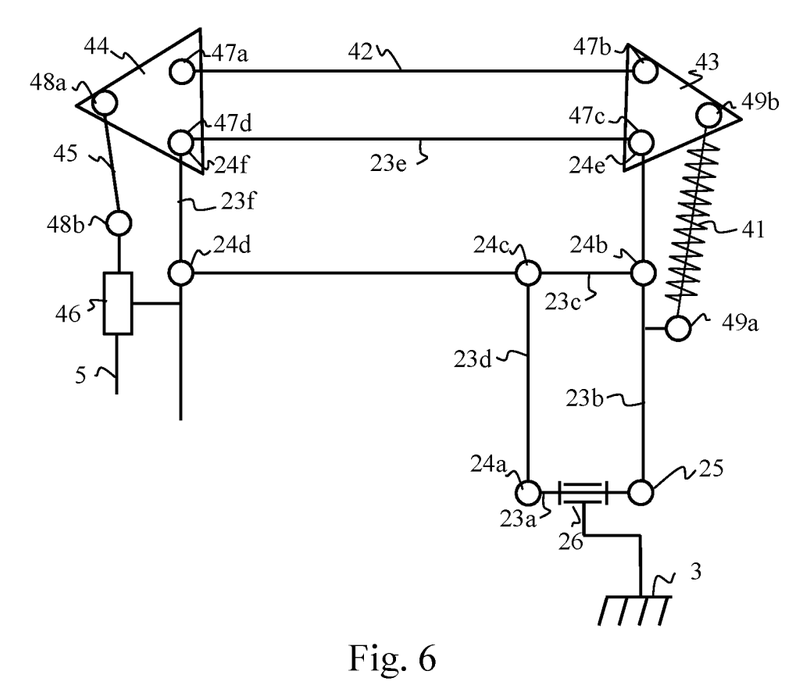
FIG. 6 illustrates a kinematic diagram of the mechanism of the robot.

FIG. 6 illustrates a kinematic diagram of the robot 1 in the plane (Oxz). The base 3 is connected to the bottom rod 23a of the arm 2 by a pivot connection 26 of axis (Ox). The rods 23a, 23b, 23c, 23d, 23e and 23f of the arm 2 form a double parallelogram and are connected to each other by pivot connections 24a, 24b, 24c, 24d, 24e and 24f of axis (Oy). The insertion/extraction system is connected to the arm 2 by the top rod 23a and the two pivot connections of axis (Oy) 47c and 47d, which are, in an example embodiment, coaxial with the respective pivot connections 24e and 24f. The top rod 24e forms, with the rod 42 and the rotary elements 43 and 44, a third parallelogram that is articulated about the pivot connections 47a, 47b, 47c and 47d. The third parallelogram thus makes it possible to transmit a rotation of a third type actuated at the rotary element 43 about the axis of the pivot connection 47c to the rotary element 44 about the axis of the pivot connection 47d. Said rotation of a third type transmitted to the rotary element 44 is transformed into a translation movement by means of a connecting rod 45 connected firstly to the rotary element 44 by a pivot connection 48a and secondly to the front rod 23f by a pivot connection 48b and a sliding connection 46. The tool 5 is connected to the connecting rod 45 by the sliding connection 46 and follows said translation movement.

The spring 41 is connected to the arm 2 by a pivot connection 49a and to the rotary element 43 of the insertion/extraction system by a pivot connection 49b. When the element 43 turns in an anticlockwise direction about the pivot connection 47c and the tool 5 is lowered, the spring 41 deforms by extending and exerts a traction at its ends on the rear rod 23b on the one hand and the rotary element 43 on the other hand. When a torque applied to the rotary element 43 in the anticlockwise direction is eliminated, the traction of the spring 41 on the rotary element 43 tends to rotate the rotary element 43 about the pivot connection 47c in the clockwise direction. The rotary element 44 then rotates in a similar manner and parallel to the element 43 about the pivot connection 47d in the clockwise direction, the connecting rod 45 transforming the rotation movement of the element 44 into an upward translation movement, which results in a raising of the tool 5.

Figure 7:
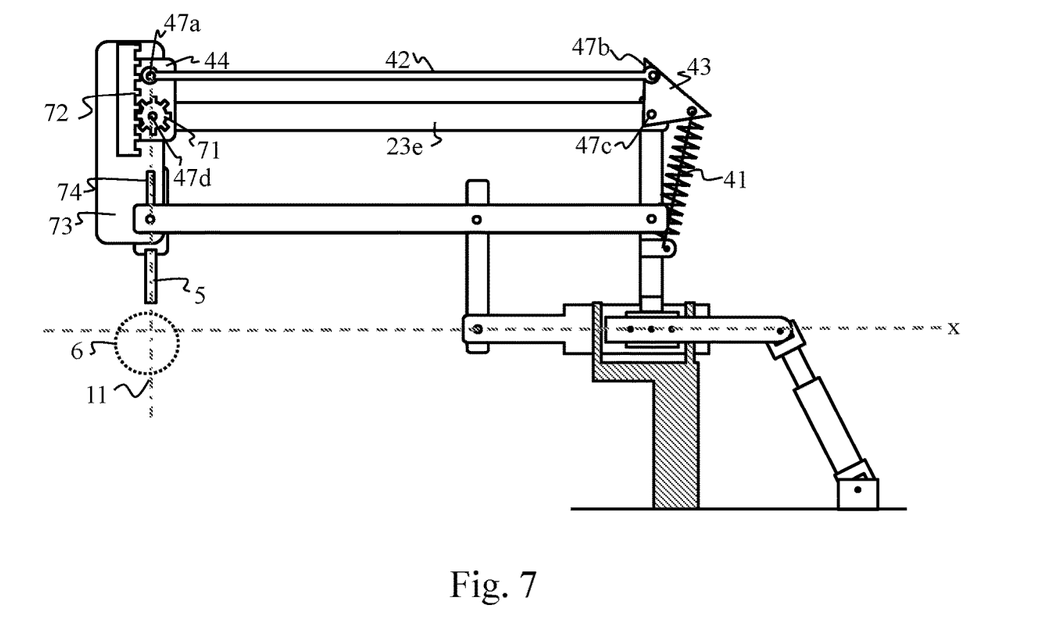
FIG. 7 schematically illustrates the robot in side view, the insertion/extraction system being presented in a raised position with the tool located outside the surgical field and comprising a toothed wheel associated with a rack.

FIG. 7 schematically illustrates an alternative embodiment of the mechanism 40b for transforming the rotation of a third type into translation. Said mechanism comprises a toothed wheel 71 attached to the rotary element 44 and centred on the axis of the pivot connection 47d. The toothed wheel 71 is connected by gearing to a rack 72, attached to a tool holder 73 so that the rotation of a third type of the toothed wheel 71 causes the translation of the tool holder 73 parallel to the insertion axis 11. The tool holder 73 is connected to the front rod 23f by a sliding connection 74 allowing a translation parallel to the insertion axis 11. The tool 5 is connected to the tool holder 73 by a connection allowing a rotation centred on the insertion axis 11 and follows the translation movement of the tool holder 73 parallel to the insertion axis 11.

The invention claimed is:

1. A surgery-assistance device comprising:
   means for offsetting a rotation of a first type and a rotation of a second type;
   a mechanism for transmitting a rotation of a third type; and
   a mechanism for transforming the rotation of the third type into a translation, said translation being enabled along an insertion axis oriented in a direction defined by the means for offsetting the rotation of the first type and the rotation of the second type, the mechanism for transmitting the rotation of the third type being connected to a first end of an elastic element, the second end of the elastic element being connected to the means for offsetting the rotation of the first type and the rotation of the second type, the mechanism for transmitting the rotation of the third type being connected to a rotary motor, the rotation of the rotary motor in a first direction causing the lowering of a tool carried by the surgery-assistance device and a first deformation of the elastic element, the rotation of the rotary motor in a second direction causing the raising of the tool (5) and a second deformation of the elastic element opposite to the first deformation, the tool remaining in a given position as long as a torque exerted by the rotary motor is maintained and, when the tool is in a lowered position and the rotary motor is not exerting any torque, the elastic element returns to an initial shape causing the raising of the tool, and in that the means for offsetting the rotation of the first type and the rotation of the second type comprise two parallelograms connected together and a device for actuating the rotation of the third type and the rotation of the second type, the actuation device generating a rotation movement of the first type, about a first axis, of a rod of a parallelogram of the two parallelograms with respect to another rod of said parallelogram, and generating a rotation movement of the second type, about a second axis, of the two parallelograms with respect to a base of the surgery-assistance device, the first axis being perpendicular to the second axis, and the rotation movements of the first type and of the second type being transmitted by the two parallelograms at an offset centre of rotation.

2. The device according to claim 1, wherein the first deformation is an elongation.

3. The device according to claim 1, wherein the actuation device comprises two other rotary motors, each of the rotations of a first and second type being actuated by one of the other two rotary motors.

4. The device according to claim 3, wherein the mechanism for transmitting the rotation of the third type comprises a belt, the rotary motor generating a rotation movement of the third type, about the third axis, of a first rotary element with respect to the means for offsetting the rotation of a third type and the rotation of the second type, the rotation movement of the third type being transmitted by the belt to a second rotary element, about a fourth axis parallel to the third axis.

5. The device according to claim 1, wherein the actuation device comprises two linear motors, the rotations of a first and second type being actuated by the conjoint action of the two linear motors.

6. The device according to claim 1, wherein the mechanism for transmitting the rotation of the third type comprises a third parallelogram, the rotary motor generating a rotation movement of the third type, about the third axis, of a first rotary element with respect to the means for offsetting the rotation of the first type and the rotation of the second type, the rotation movement of the third type being transmitted by the third parallelogram to a second rotary element, about a fourth axis parallel to the third axis.

7. The device according to claim 1, wherein the mechanism for transforming the rotation of the third type into a translation comprises a connecting rod, the head of the connecting rod being connected to the mechanism for transmitting the rotation of the third type and the foot of the connecting rod is connected to the tool and to the means for offsetting the rotation of the first type and the rotation of the second type, and, when the rotation movement of the third type is transmitted to the head of the connecting rod, the foot of the connecting rod transmits to the tool a translation movement along the insertion axis.

8. The device according to claim 1, wherein the mechanism for transforming the rotation of the third type into a translation comprises a toothed wheel connected to the mechanism for transmitting the rotation of the third type and comprises a rack secured to a tool holder to which the tool is connected, the toothed wheel being connected to the rack by gearing so that, when the toothed wheel begins to move in the rotation of the third type, the tool makes a translation movement along the insertion axis.

9. The device according to claim 1, wherein the means for offsetting the rotation of the first type and the rotation of the second type are connected to a movable base, the movable base being able to be moved and secured to an operating table in accordance with three translation axes perpendicular to each other.

10. The device according to claim 1, furthermore comprising a mechanism for rotating the tool about the insertion axis.

11. The device according to claim 1, wherein the tool is an endoscope for assisting ear and sinus surgery.

12. The device according to claim 1, furthermore comprising a control means configured to be actuated by an individual and cancelling out the torque exerted by the rotary motor so that, if the tool is in a lowered position, the elastic element returns to the initial shape causing the raising of the tool.

\* \* \* \* \*